(12) United States Patent
Goble et al.

(10) Patent No.: US 6,582,427 B1
(45) Date of Patent: Jun. 24, 2003

(54) ELECTROSURGERY SYSTEM

(75) Inventors: Colin C. O. Goble, Penarth (GB); Francis E Amoah, Cardiff (GB); Nigel M Goble, Cardiff (GB)

(73) Assignee: Gyrus Medical Limited, Wales (GB)

( * ) Notice: Subject to any disclaimer, the term of this patent is extended or adjusted under 35 U.S.C. 154(b) by 0 days.

(21) Appl. No.: 09/517,631

(22) Filed: Mar. 3, 2000

Related U.S. Application Data
(60) Provisional application No. 60/141,261, filed on Jun. 30, 1999.

(30) Foreign Application Priority Data

Mar. 5, 1999 (GB) .............................................. 9905210

(51) Int. Cl.$^7$ ............................................. A61B 18/18
(52) U.S. Cl. .............................. 606/37; 606/34; 606/41; 606/38
(58) Field of Search ...................... 606/32–41

(56) References Cited

U.S. PATENT DOCUMENTS

| | | | |
|---|---|---|---|
| 3,699,967 A | | 10/1972 | Anderson |
| 3,903,891 A | * | 9/1975 | Brayshaw ..................... 606/27 |
| 4,494,539 A | | 1/1985 | Zenitani et al. |
| 4,534,347 A | | 8/1985 | Taylor |
| 4,583,556 A | | 4/1986 | Hines et al. |
| 4,641,649 A | | 2/1987 | Walinsky et al. |
| 4,712,544 A | | 12/1987 | Ensslin |
| 4,825,880 A | | 5/1989 | Stauffer et al. |
| 5,150,717 A | * | 9/1992 | Rosen et al. ................... 606/33 |
| 5,267,998 A | | 12/1993 | Hagen |
| 5,423,809 A | * | 6/1995 | Klicek .......................... 606/38 |
| 5,630,426 A | | 5/1997 | Eggers et al. |
| 5,669,904 A | | 9/1997 | Platt, Jr. et al. |
| 5,683,382 A | | 11/1997 | Lenihan et al. |
| 5,762,626 A | | 6/1998 | Lundquist et al. |
| 5,954,686 A | | 9/1999 | Garito et al. |
| 6,224,593 B1 | * | 5/2001 | Ryan et al. ................... 606/33 |
| 6,245,065 B1 | | 6/2001 | Panescu et al. |

FOREIGN PATENT DOCUMENTS

| | | |
|---|---|---|
| EP | 0150253 | 8/1985 |
| EP | 0423757 | 4/1991 |
| GB | 1537235 | 12/1978 |
| GB | 2105200 | 3/1983 |
| GB | 2285750 | 7/1995 |
| WO | WO 95/26686 | 10/1995 |
| WO | WO 98/35618 | 8/1998 |

* cited by examiner

Primary Examiner—David M. Shay
(74) Attorney, Agent, or Firm—Oliff & Berridge, PLC.

(57) ABSTRACT

An electrosurgery system includes an electrosurgical generator (10) coupled to or part of an electrosurgical instrument, the generator being operable to generate electrosurgical power in low frequency (typically at 1 MHz) and high frequency bands (typically at 2.45 GHz) either simultaneously or individually the generator includes a load-responsive control circuit which, in one mode, causes power to be generated predominantly at 1 MHz when the load impedance is high and predominantly at 2.45 MHz when it is low. This allows automatic switching between cutting and coagulation operation. In one embodiment, the instrument includes a gas plasma generator operating such that an ionizable gas is energized in a gas supply passage by the 2.45 GHz component to form a plasma stream which acts as a conductor for delivering the 1 MHz component to a tissue treatment outlet of the passage. (FIG. 4).

5 Claims, 9 Drawing Sheets

ELECTROSURGERY SYSTEM

This nonprovisional application claims the benefit of U.S. Provisional Application No. 60/141,261, filed Jun. 30, 1999.

This invention relates to a radio frequency electrosurgery system and a method of operating an electrosurgical inset at UHF frequencies.

It is known to use a needle or narrow rod electrode for cutting tissue in monopolar electrosurgery at frequencies in the range of 300 kHz to 3 MHz. An electrosurgical signal in this frequency range is applied to the electrode, and the electrical current path is completed by conduction through tissue to an earthing plate secured to the patients body elsewhere. The voltage applied to the electrode must be sufficiently high to cause arcing and consequent thermal rupture so that tissue adjacent the needle is ablated or vaporised.

At lower power levels, coagulation of the tissue can be achieved, i.e. without arcing, due to thermal dissipation of energy in the tissue adjacent the electrode, However, with a narrow electrode as commonly used for tissue cut, desiccation of the tissue immediately adjacent the electrode and build-up of desiccated material on the electrode itself constitutes a high-impedance barrier to further coagulation. Spatula-shaped electrodes have been produced to overcome the difficulty in providing a dual-purpose electrode, i.e. one suitable for both cutting and coagulation. The designer's intention is that the edge of the electrode is used for cutting, whereas the flat surface is used for coagulation. However, coagulation with such an electrode tends to be imprecise due to the size of the flat surface, with the result that a large thermal margin is produced.

It is an object of the invention to provide a means of achieving both tissue cutting and coagulation with a single electrode assembly.

According to this invention, there is provided an electrosurgery system comprising an electrosurgical generator, a feed structure and an electrode assembly, the electrode assembly having at least one active electrode and at least one adjacent return electrode each of which is coupled to the generator via the feed structure, wherein the generator and feed structure capable of delivering radio frequency (r.f.) power to the active and retain electrodes in lower and upper frequency ranges, the upper range containing frequencies at least three times the frequencies of the lower frequency range. The lower frequency range may extend from 100 kHz to 100 MHz preferably 300 kHz to 40 MHz, and the upper frequency range may extend from 300 MHz to 10 GHz, preferably above 1 GHz, with operating frequencies in the upper and lower ranges having a frequency ratio of 5:1 or greater. Typically, the generator is arranged such that the r.f. power delivered in the upper frequency range is at a fixed frequency which is at least ten times the frequency of power delivered in the lower frequency range. Indeed, a fixed frequency of 2.45 GHz in the upper frequency range is preferred.

The preferred system allows simultaneous delivery of lower and upper frequency range components to the electrodes to provide a combination of medium or low frequency tissue cutting, vaporisation or ablation together with coagulation of surrounding tissue to a degree dependent upon the amplitude of the component in the upper frequency range.

For tissue cutting, vaporisation or ablation the system preferably operates in a monopolar mode with a separate earthing electrode applied to the outside of the patient's body, whilst coagulation occurs in a quasi-bipolar mode whereby the return current path in the upper frequency range runs from the tissue adjacent the operation site to the return electrode of the electrode assembly due to capacitive coupling. It will be understood that the system may allow selection of power delivery either in the lower frequency range or the upper frequency range depending upon the kind of treatment required. This selection may be performed manually by the surgeon or automatically in the manner to be described below. In addition, power may be supplied in both frequency ranges simultaneously to obtain a blended cutting and coagulation effect, the two components being linearly added or otherwise combined in a single signal feed structure.

In a particularly preferred embodiment of the invention, the generator includes a control circuit responsive to electrical load and operable to cause the delivered power to have a predominant frequency component in the lower frequency range when the load impedance is in an upper impedance range, and to have a predominant frequency component in the upper frequency range when the load impedance is in a lower impedance range. In this way, it is possible to cut, ablate or vaporise living tissue (i.e. causing cell rupture) with the lower frequency range component but also to bring about efficient coagulation when a very low load impedance is detected, indicating the presence of electrolytic fluid such as blood from a blood vessel, requiring coagulation. The system reverts to predominantly low frequency operation once the impedance has risen above a predetermined threshold following coagulation.

When electrical load impedance is used as the control stimulus, a signal representative of load impedance being compared with a reference signal, the reference signal may have different levels depending on whether the generator is to be switched from a predominant low frequency component to a predominant high frequency component or vice versa. In other words, different load impedance thresholds may be selected when operating in the lower frequency range or the upper frequency range respectively.

A composite signal having components from both frequency ranges may be produced by combining (e.g. adding) the signals from two generator stages, one operating in the region of, say, 1 MHz and the other operating at 2.45 GHz. Both generator stages may be in a single supply unit coupled to an electrosurgical instrument which consists of a handpiece mounting the electrode assembly so that, for instance, the two frequency components are fed from the supply unit to the handpiece by common delivery means such as a low loss flexible coaxial cable. Alternatively, the generator stage producing the UHF frequency component may be located in the handpiece to reduce transmission losses and radiated interference, the signal combination being performed within the handpiece as well.

For dual-purpose operation, i.e. cutting and coagulation, an electrode assembly having a needle-like active electrode is preferred.

Typically, the electrode assembly is at the distal end of a rigid or resilient coaxial feed forming the above-mentioned feed structure. To reduce extraneous UHF radiation, an isolating choke element in the form of a conductive quarter-wave stub or sleeve may be mounted to the outer supply conductor of the coaxial feed in the region of the distal end. As stated above, the active electrode may take the form of a rod or pin projecting from the coaxial feed distal end. The return electrode may be a conductive sleeve, plate or pad connected to the outer supply conductor at the feed distal end and extending proximally over the outer conductor but spaced from the latter so that the active electrode rod and the return electrode sleeve, plate or pad together form an axially oriented dipole at the operating frequency of the generator in the upper frequency range. Alternatively, the return electrode simply takes the form of a distal end portion of the feed outer conductor located distally of the choke. The return electrode may be covered with an electrically insulative layer in order that, when the active electrode is applied to tissue, the return electrode, being set back from the active electrode so as normally to be spaced from the tissue, acts as a capacitive element forming part of a capacitive return path between the treated tissue and the return supply conductor of the feed.

In an alternative embodiment in accordance with the invention, the electrode assembly includes a gas supply passage and the active electrode is located within the passage where it acts as a gas-ionising electrode. In this case, the active electrode acts as a low- to high-impedance transformer at the operating frequency of the generator in the upper frequency range, producing an intense electric field in the space between the distal end portion of the active electrode and the return electrode. Accordingly, when there is an ionisable gas in the passage, the major part of the power delivered to the electrode assembly in the upper frequency range is dissipated in the passage. In the lower frequency range no transforming effect occurs and the frequency component in the lower frequency range is, instead, delivered to the tissue to be treated by the ionised gas plasma which, in effect, acts as a monopolar gaseous electrode. Use of a UHF frequency component as a plasma generator and a lower frequency component for electrosurgery allows independent control of plasma generation and electrosurgical power delivery, thereby avoiding the disadvantage of known single r.f. source gas plasma electrosurgery devices. Typically, in such a prior device the ability of the source to deliver current through the plasma is severely hampered due to the requirement for high peak voltages when using low frequencies (i.e. typically, less than 1 MHz).

The invention will now be described by way of example and with reference to the drawings in which.

The preferred embodiments of the present invention are applicable mainly to the performance of electrosurgery upon tissue in a gaseous environment using a dual electrode instrument having active and return electrodes situated at the distal end of an instrument shaft. The active electrode is applied directly to the tissue. The return electrode does not contact the tissue being treated, but is normally adjacent the tissue surface where it is capacitively coupled to the tissue at UHF frequencies.

Figure 1:
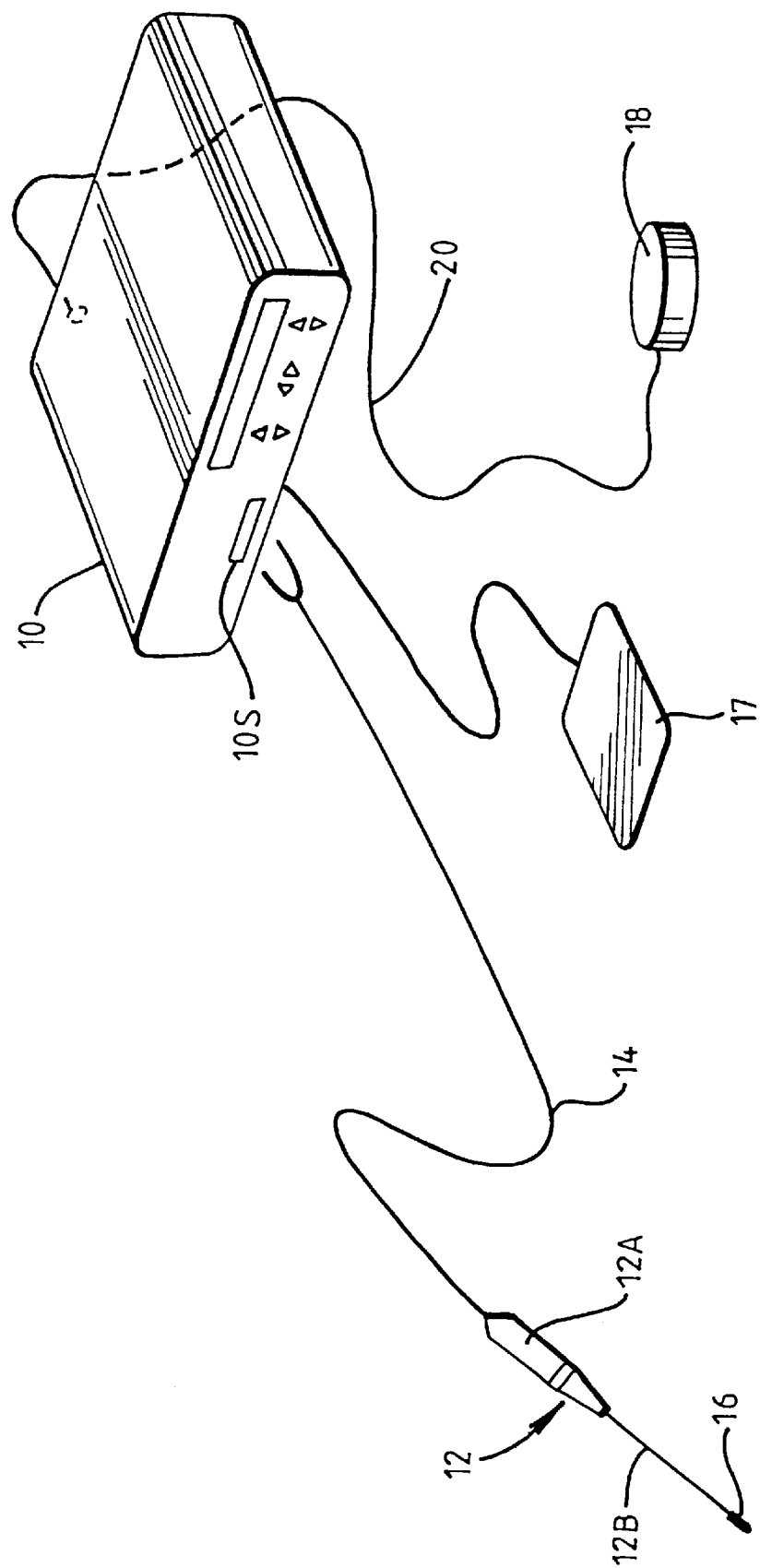
FIG. 1 is a diagram showing an electrosurgical system in accordance with the invention.

A system incorporating such an instrument is shown in FIG. 1. Referring to FIG. 1, the system has a electrosurgical supply unit 10 with an output socket 10S providing a radio frequency (r.f.) output for the electrosurgical instrument 12 via a flexible cable 14. Instrument 12 has a handpiece 12A and, mounted to the handpiece, an instrument shaft 12B having an electrode assembly 16 at its distal end. A patient return pad 17 is also connected to the supply unit 10. Activation of the supply unit may be performed from the handpiece 12A via a control connection in cable 14, or by means of a foot switch 18 connected separately to the rear of the supply unit 10 by a foot switch connection cable 20.

Instrument shaft 12B constitutes a feed structure for the electrode assembly 16 and takes the form of a rigid coaxial feed having an inner conductor and an outer supply conductor made with rigid material constructed as a resilient metal tube or as a plastics tube with a metallic coating. The distal end of the feed structure appears in FIG. 2 from which it will be seen that the inner conductor 22 has an extension which projects beyond the outer conductor 24 as a rod 26 forming an axially extending active electrode of a diameter typically less than 1 mm. Where they are surrounded by the outer supply conductor 24, the inner supply conductor 22 and the active electrode 26 are encased in a coaxial ceramic or high-temperature polymer sleeve 28 acting as an insulator and as a dielectric defining the characteristic impedance of the transmission line formed by the coaxial feed.

The return electrode is formed as a coaxial conductive sleeve 30 surrounding a distal end portion of the outer supply conductor 24 with an intervening annular space 31. An connection between the return electrode 30 and the outer supply conductor 24 is formed as an annular connection 30A at one end only, here the distal end, of the return electrode 30 such that the projecting portion of the active electrode 26 and the return electrode 30 together constitute an axially extending dipole with a feed point at the extreme distal end of the coaxial feed. This dipole 26, 30 is dimensioned to match the load represented by the tissue and air current path to the characteristic impedance of the feed at or near 2.45 GHz.

Located proximally of the electrode assembly formed by active electrode 26 and return electrode 30 is an isolating choke constituted by a second conducive sleeve 32 connected at one of its ends to the outer supply conductor 24 by an annular connection 32A. In this instance, the annular connection is at the proximal end of the sleeve. The sleeve itself has an electrical length which is a quarter-wavelength ($\lambda/4$) at 2.45 GHz or thereabouts, the sleeve thereby acting as an balun promoting at least an approximately balanced feed for the dipole 26, 30 at that frequency.

The projecting part of the active electrode 26 has a length in the region of 10 mm while the return electrode 30 is somewhat greater than 10 mm in length. The reason for this difference in length is that the relative dielectric constant of living tissue is higher than that of air, which tends to increase the electrical length of the active electrode for a given physical length. The electrode assembly 16 and choke 32 are configured to provide an electrical impedance match with the tissue being treated and, advantageously, a mismatch to the impedance of free space, so that power transmission from the electrode assembly is minimised when the active electrode is removed from tissue whilst an electrosurgical voltage is still being applied at 2.45 GHz.

Sleeve 32 has an important function insofar as it acts as an isolating tap isolating the outer supply conductor 24 of the feed structure from the return electrode 30, largely eliminating r.f. currents at 2.45 GHz on the outside of the outer supply conductor 24. This also has the effect of constraining the electric field which results from the application of a voltage at 2.45 GHz between the active electrode and the return electrode, as seen in FIG. 3.

Figure 2:
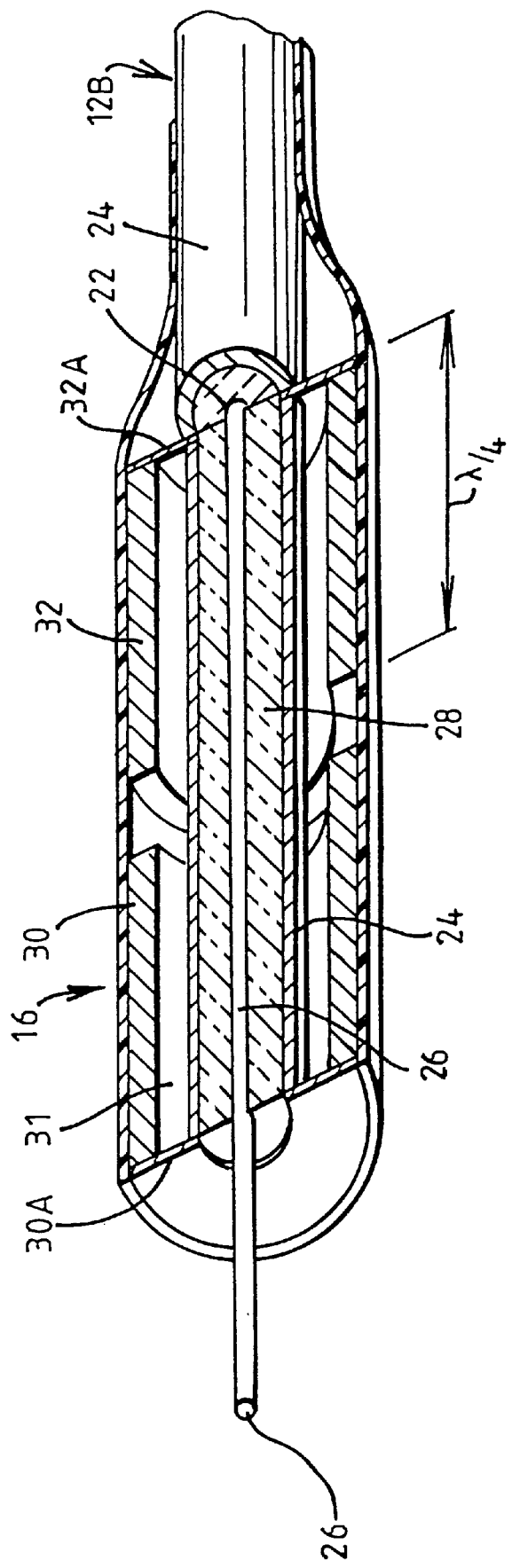
FIG. 2 is a diagrammatic cult away perspective view of an electrode assembly and associated feed structure.
Figure 3:
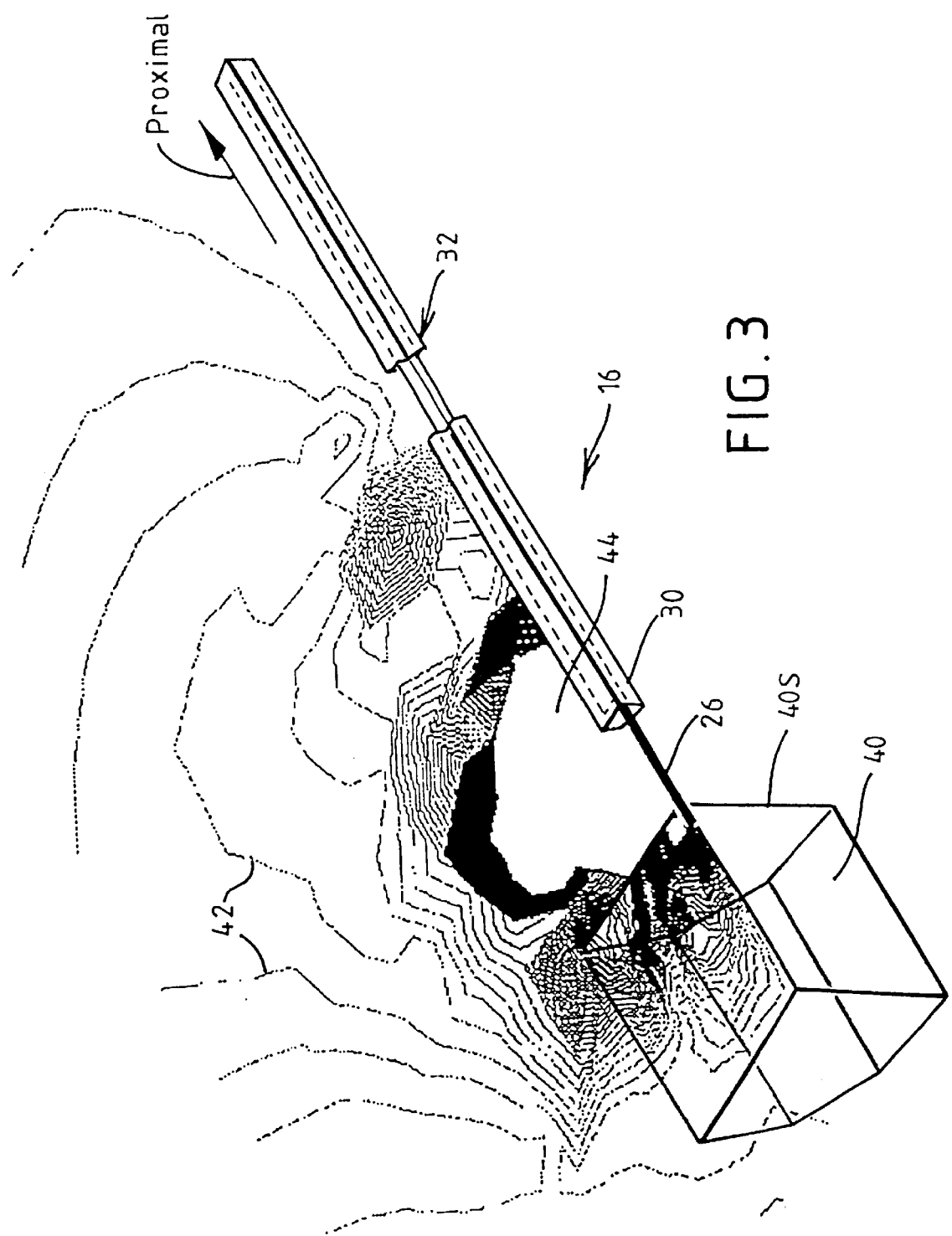
FIG. 3 is a diagram showing a simulation of the electric field pattern obtainable with the electrode assembly of FIG. 2.

FIG. 3 is a computer-generated finite element simulation of the electric (E) field pattern produced by the electrode assembly 16 and choke 32 of FIG. 2 when energised via the coaxial feed 12B at 2.45 GHz. It should be noted that the components of the electrode assembly and the sleeve 32 are shown quartered in FIG. 3 (i.e with a 90° sector cross-section). The active electrode 26 is shown with its tip in contact with a body 40 of tissue. The pattern 42 of E-field contours in a plane containing the axis of the electrode assembly illustrates the marked concentration of E-field in the space 44 surrounding the active electrode 26 and the distal part of the return electrode 30 immediately adjacent the tissue surface 40S. Proximally of this space, the E-field intensity is much reduced, as will be seen by the relatively wide spacing of the contours. (It should be noted that the region 44 of greatest intensity appears as a white area in the drawing. In this region and the immediately surrounding region the contour lines are too closely spaced to be shown separately.) The presence of an intense E-field region between the distal end of the return electrode 30 and the tissue surface 40S is also indicative of capacitive coupling between these two surfaces at the frequency of operation (which is 2.45 GHz in the simulation of FIG. 3). Localisation of the E-field in this manner also has the effect of reducing radiated loss in comparison with an arrangement in which intense field regions exist further from the tissue surface 40S, with the effect that radiated loss is minimised.

Referring back to FIG. 2, it will be understood that the feed structure makes use of a coaxial feed rather than a waveguide to transmit power to the electrode assembly from the handpiece and, indeed, as shown in FIG. 1, there is a flexible cable between the handpiece 12 and the electrosurgical supply unit 10. Use of coaxial feeders rather than waveguides in both cases allows the transmission of voltage components of widely spaced frequencies in a single transmission fine. This also provides the advantage of a flexible connection between the handpiece 12 and the supply unit 10. Dielectric losses in the cable 14 are mitigated by selection of a cable with a low density, partly air-filled dielectric structure. A further reduction in dielectric loss can be obtained by increasing the diameter of the cable. Such increased diameter need not be used over the whole length of the cable 14. Indeed, a smaller diameter may be retained near the handpiece to retain flexibility of movement.

The ability to feed different voltage components at different frequencies from the supply unit to the handpiece in a single transmission line has advantages related to the main aspect of the present invention which is the provision of means for delivering r.f. power to the electrode assembly in lower and upper frequency ranges, the upper range containing frequencies at least five times the frequencies of the lower frequency range. Thus, the supply unit may include generator parts generating electrosurgical signals at, for instance) 1 MHz and 2.45 GHz respectively to suit different operation site conditions and surgical requirements. In the preferred embodiments of the invention, these different components are supplied simultaneously through cable 14 to the handpiece 12 and electrode assembly 16.

Details of the electrosurgical generator for delivering electrosurgical power in this way will now described with reference to FIGS. 4 to 9.

Figure 4:
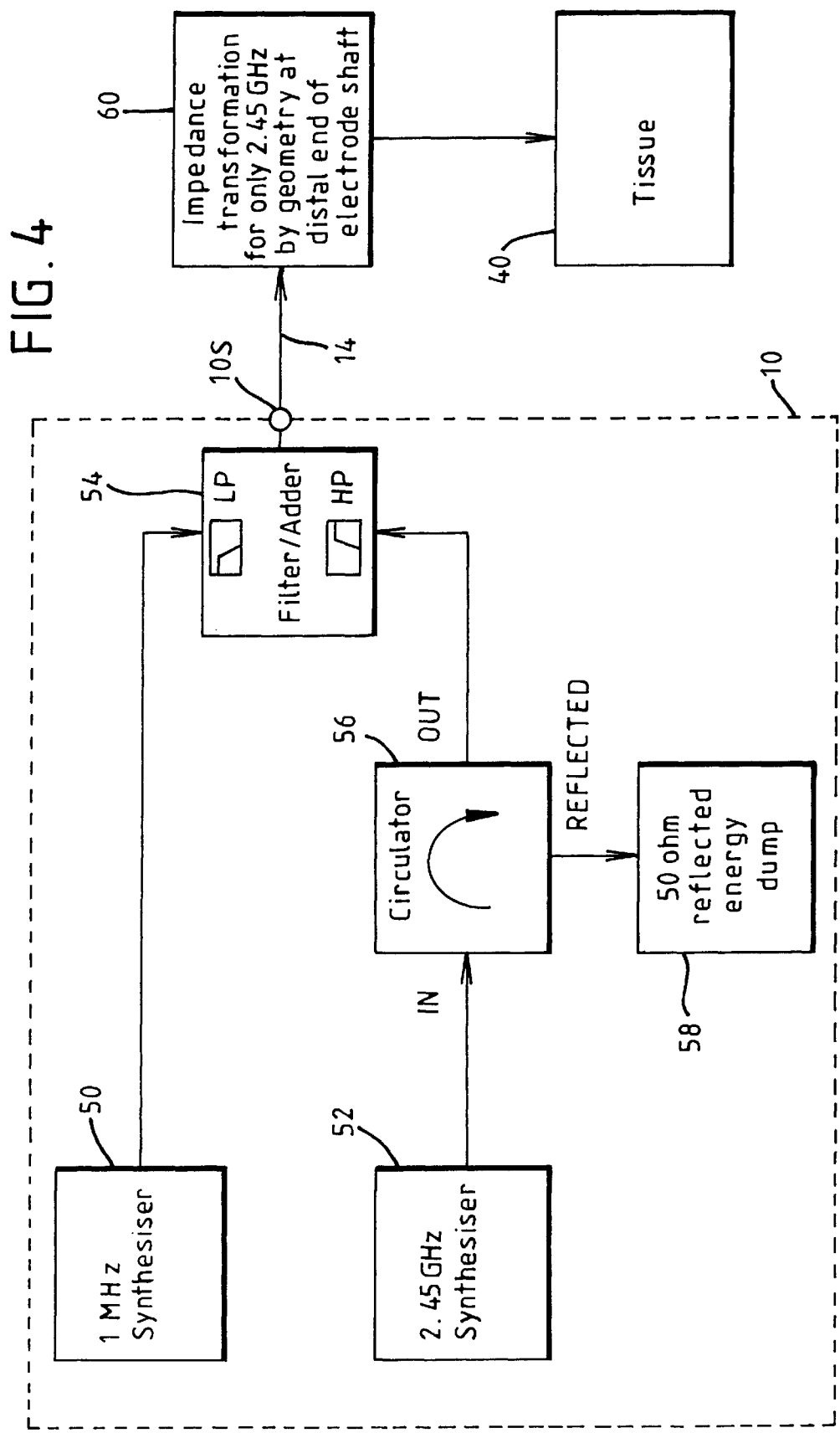
FIG. 4 is an electrical block diagram of the system of FIG. 1.

Referring to FIG. 4, the supply unit 10 contains separate 1 MHz and 2.54 GHz synthesisers 50, 52 the output signals of which are summed in an adder stage 54 having low- and high-pass filters coupled to inputs arranged to receive the 1 MHz and 2.45 GHz signals respectively, as shown. A circulator 56 connected in series between the 2.45 GHz synthesiser 52 and the adder 54 serves to provide a 50 ohm source impedance for synthesiser 52 under conditions of varying load impedance, reflected power being dissipated in a 50 ohm reflected energy sink or dump 58, also connected to the circulator 56.

At the output of the adder 54 a composite signal consisting principally of the two frequency components at 1 MHz and 2.45 GHz is delivered to the output socket 10S of the supply unit and thence via cable 14, which is typically in the region of three meters long, to the handheld instrument, represented in FIG. 4 by an impedance transformer 60 operable at 2.45 GHz, and thereafter to the tissue 40 under treatment.

Figure 5:
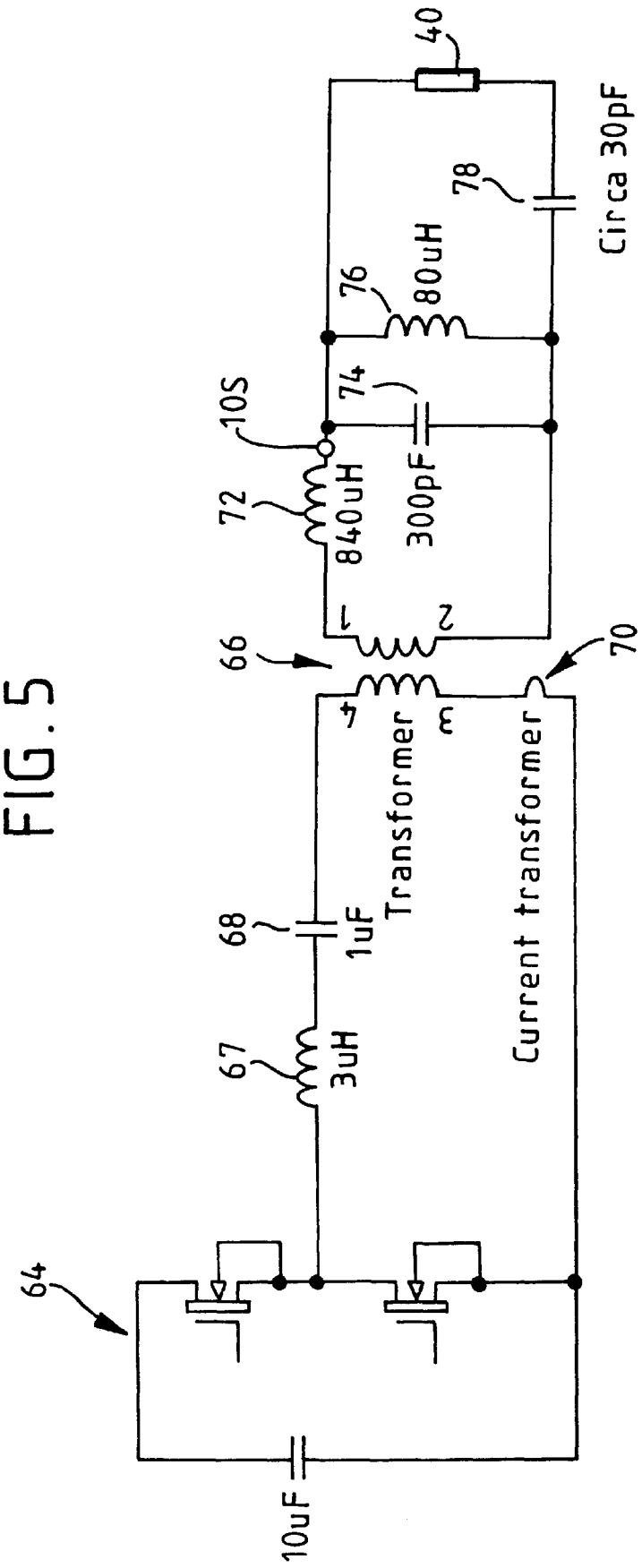
FIG. 5 is a circuit diagram of a low frequency part of the generator used in the system of FIG. 4.

Referring to FIG. 5, the 1 MHz synthesiser has a push-pull output stage 64 which drives an output transformer 66 via a current limiting inductor 67 of 3 $\mu$H and a series coupling capacitor 68 of 1 $\mu$F. Included in the primary circuit of the transformer 66 is a shunt current transformer 70 having an output winding (not shown) for monitoring the output current of the synthesiser at 1 MHz The transformer secondary winding is coupled to the output 10S through a tuning inductance 72 of 840 $\mu$H which resonates with the capacitance of the cable 14 and other components on the secondary side of the transformer 66. In this example the cable has an inherent shunt inductance of about 80 $\mu$H and the series capacitance 78 between the return electrode and the tissue being treated is in the region of 30 pF. The tissue is shown as a resistance 40. Those skilled in the art will understand that at 1 MHz, series inductance 72 and capacitance 78 can resonate so as to act as a short circuit, thereby coupling the load (tissue resistance 40) directly to the transformer secondary under matched conditions. The effect of the series inductance 67 in the primary circuit is to limit the secondary current at 1 MHz typically to 50 mA. The capacitance 78 is larger than 30 pF of the patient-attached return pad 17 (see FIG. 1) is used such that, at 1 MHz, the system is used in a monopolar mode.

It will be understood that the filter/adder circuitry shown in FIG. 4 has been omitted from FIG. 5 for clarity.

Figure 6:
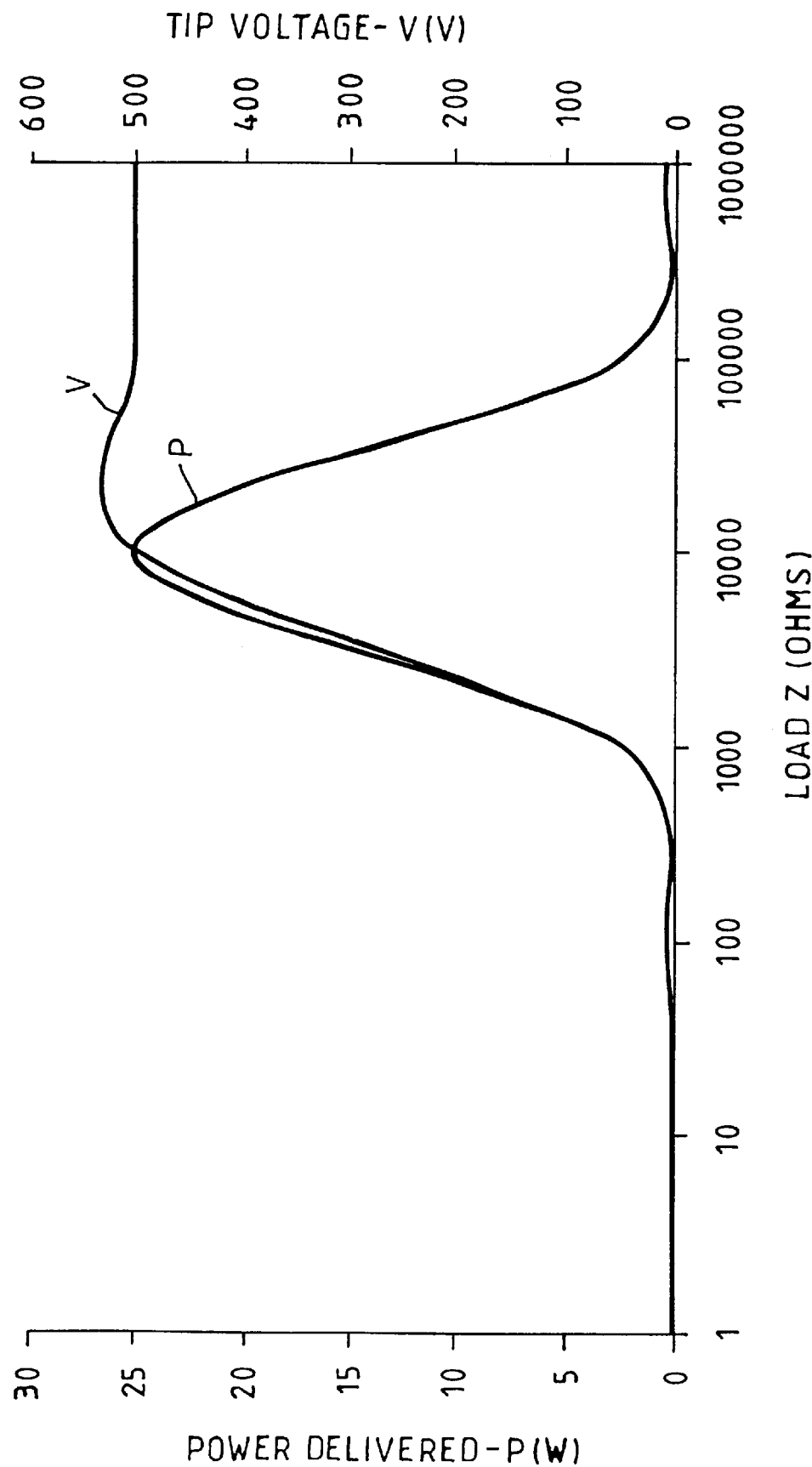
FIG. 6 is a graph showing the variation of delivered power and voltage obtained from the generator part of FIG. 5.

As will be seen from the graph of FIG. 6, the arrangement described above with reference to FIG. 5 yields maximum power transfer to the tissue when the tissue impedance is in the region of 10 k ohms. At 1 k ohm and below, both the delivered power and the output voltage are comparatively low, representing a stall condition. Stalling occurs, typically, when the electrode assembly encounters an electrolyte, such as when a blood vessel is cut. This condition is detected in a manner which will now be described.

Figure 7:
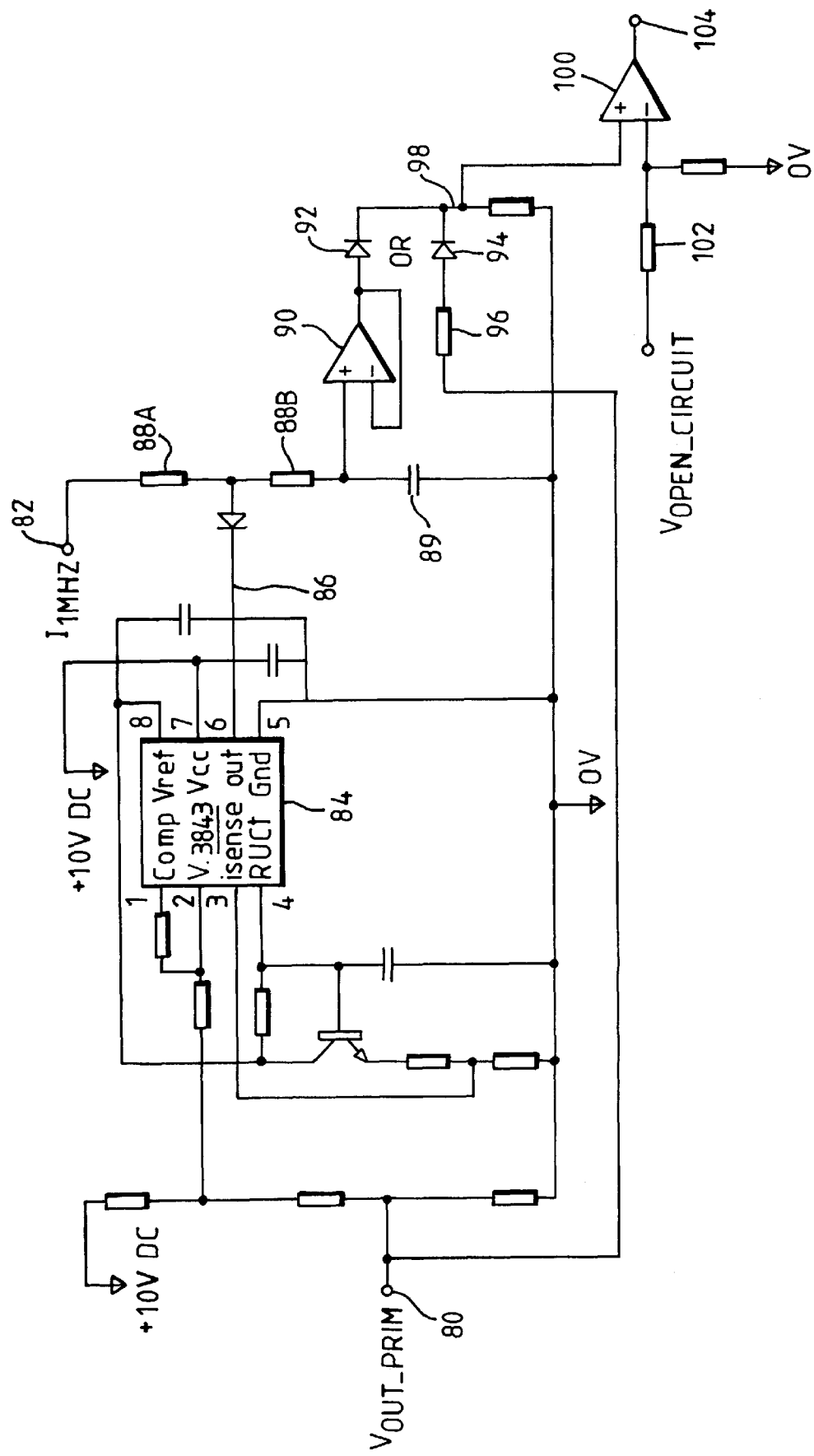
FIG. 7 is a circuit diagram of a generator control circuit.

Referring to FIG. 7, a 1 MHz stall detector, forming part of the 1 MHz synthesiser 50 shown in FIG. 4, has voltage and current inputs 80 and 82 respectively. In the first instance, the stall detector applies the voltage from the primary winding of the transformer 66 (see FIG. 5) to a pulse width modulation chip 84 to produce a pulsed output signal having a pulse width which varies according to the voltage supplied at input 80. At input 82, a voltage proportional to the current in the primary winding of transformer 66, as sensed by the current transformer 70, is supplied to a potential divider 88A, 88B, the tap of the divider being connected to the output line 86 of the pulse width modulation chip 84. Accordingly, the voltage applied to buffer circuit 90, smoothed by capacitor 89, is equivalent to the pule width modulation output on output line 86, scaled according to the level of the transformer primary current. In other words, the signal applied to buffer 90 represents the product of the transformer primary voltage and primary current, i.e. the delivered power at 1 MHz.

Thus, the signal at the output of buffer 90 is proportional to power, and is delivered to one input of an OR-gate formed by diodes 92, 94 which receives, at its other input, the voltage applied to input 80. Accordingly, the signal at the output 98 of the OR-gate is low only when both the delivered power at 1 MHz and the output voltage at 1 MHz are low, i.e. in accordance with the power and voltage characteristics shown in FIG. 6 when the load impedance is less than a few kilohms, and typically less than 1 k ohm. An output comparator circuit 100 is used to compare the output voltage from the OR-gate 92, 94 with a reference voltage applied to input 102, repenting a reference value of the voltage obtained from the push-pull pair 64 (See FIG. 5) in open-circuit conditions. The resulting output at the detector output 104 is a control signal for enabling the 2.45 GHz synthesiser 52 shown in FIG. 4.

Figure 8:
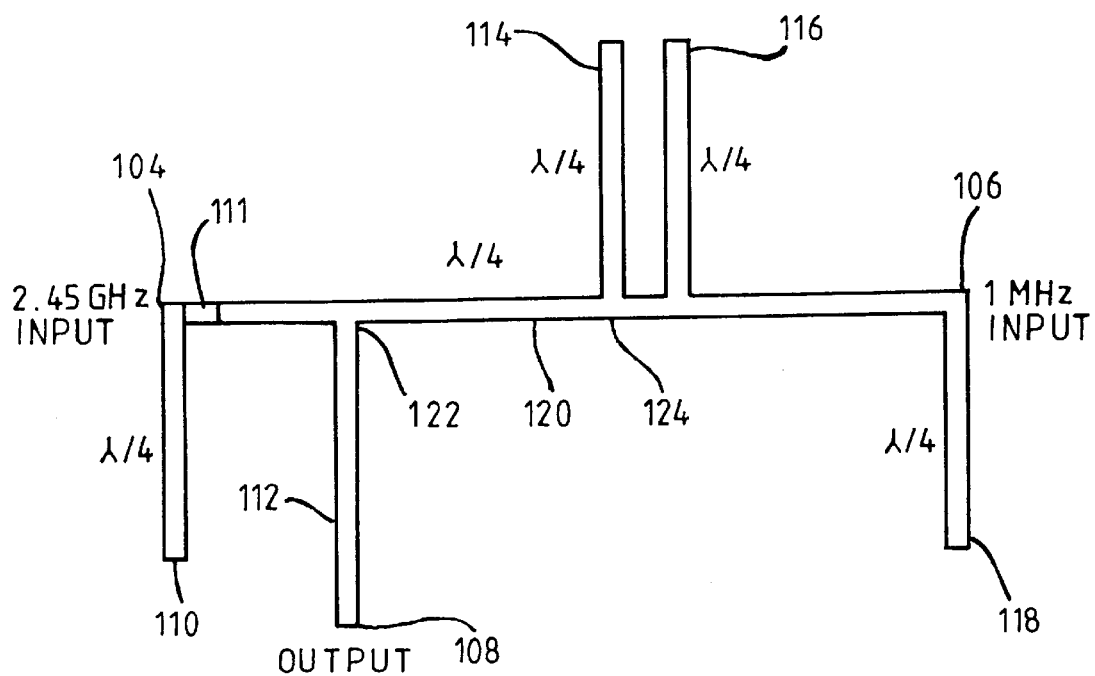
FIG. 8 is a microstrip layout for a mixer holding the signs obtained from the low and high frequency part of the generator.

The adder 54 is formed as a microstrip device, as shown in FIG. 8. This is a 3-port device having a first input port 104 for the UHF signal from the 2.45 GHz generator part and a second input port 106 for the low frequency signal from the 1 MHz generator parts The device allows the UHF signal to be transmitted to an output port 108 with little loss whilst being isolated from the low frequency input port 106. Similarly, the low frequency signal applied to port 106 is transmitted to the output port 108 with low loss whilst being isolated from the UHF input port 104 a quarter wave ($\lambda/4$) short circuit stub 110 and series capacitor 111 at the UHF input port 104 are transparent to the signal applied at input port 104, which is thereby transmitted to the output port 108 via an output limb 112. Between the output limb 112 and the low frequency input 106 are three $\lambda/4$ open circuit stabs 114, 116, 118, the first 114 of these being spaced from the output limb 112 by a series $\lambda/4$ section 120. These open circuit stubs 114, 116, 118 reactively attenuate hew 2.45 GHz signal to isolate it from the low frequency input 106. The base of the output limb 122 constitutes a sum injunction 112 and the $\lambda/4$ length of the line section 120 extends from this junction 112 to the base 124 of the first open circuit stub 114.

The open circuit stubs 114, 116, 118 are transparent to the 1 MHz signal, whereas the series capacitor 111 and the short circuit stub 110 reactively attenuate the 1 MHz signal in order to isolate the UHF input port 104 at 1 MHz.

It will be appreciated that the $\lambda/4$ components described above may, instead, have an electrical length which is any odd-number multiple of $\lambda/4$. Here, $\lambda$ is the wavelength of the applied UHF (2.45 GHz) signal in the microstrip medium.

Figure 9:
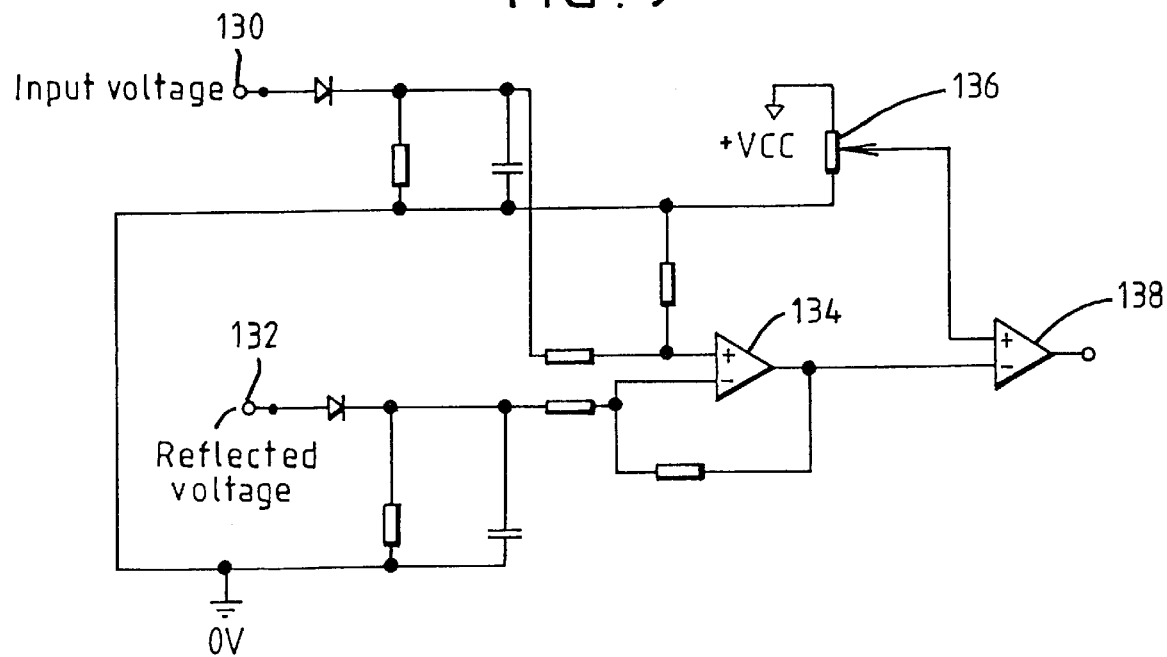
FIG. 9 is a circuit diagram for a power control circuit forming a portion of the high frequency generator part.

The 2.45 GHz synthesiser includes a power control circuit as shown in FIG. 9. Referring to FIG. 9, the power control circuit has two inputs 130, 132 coupled to the input and the "reflected" power output of the circulator 56 (see FIG. 4) respectively. The reflected voltage applied to input 132 is subtracted from the input voltage supplied to 130 in comparator 134 and the resulting difference value compared with a reference voltage set by potentiometer 136 in an output comparator 138 to produce a switching signal for limiting the power output to a threshold value set by the user (or set automatically using a microprocessor controller forming part of the supply unit). Different power settings may be used depending upon the size of the electrode assembly connected to the handpiece and environment.

It will be appreciated that electrosurgical power may be delivered from the supply unit 10 shown in FIG. 1 either exclusively at 1 MHz or exclusively at 2.45 GHz for predominantly tissue vaporisation or thermal tissue coagulation respectively. In addition, power may be delivered at both frequencies simultaneously on the basis of a user-defined combination depending upon the characteristics of the tissue being treated. A third mode of operation is an auto-detection mode using the stall detection circuit described above with reference to FIG. 6, such that either of the two components predominate in a composite output voltage waveform, according to tissue impedance. In the latter case, the user typically selects a tissue vaporisation mode for predominant tissue cleaving or vaporisation, in which mode the 245 GHz component is enabled only when the tissue being treated presents a very low impedance. As mentioned above, this typically indicates the presence of an electrolyte such as blood from a blood vessel. Under these circumstances, the UHF component (i.e. the 2.45 GHz component) of the composite voltage waveform provides coagulation and/or desiccation of the tissue in the region of blood loss, the generator continuing in that mode until the detected tissue impedance rises again, whereupon the UHF component is disabled and treatment continues again exclusively at 1 MHz.

As described above, detection of low tissue impedance in these circumstances can be achieved by comparison of voltage and current amplitudes at the output of the 1 MHz source, prior to the adder 54 shown in FIG. 4. To avoid a low impedance detection output occurring as a result of reactive loading between the generator and the tissue being treated, the detector circuit may be modified to generate a signal representative of $(V \cos \phi)/I$, where V is the magnitude of the 1 MHz voltage component, I is the magnitude of the 1 MHz current component, and $\phi$ the phase angle between the said voltage and current.

It should be noted that detection of low power delivery at 1 MHz as described above with reference to FIG. 7 makes use of a signal representative of the real power delivered to the load, scaled by the voltage that would be obtained from the 1 MHz synthesiser with an open circuit output.

In an alternative embodiment, not shown in the drawings, the UHF (2.45 GHz) synthesiser 52 shown in FIG. 4 may be installed in the handpiece 12 together with the circulator 56, energy dump 58, and adder 54. This has the advantage that the cable 14 (see FIG. 1) between the supply unit and the handpiece 12 may be an inexpensive smaller diameter component A d.c. power supply for the UHF synthesiser is also required, and may be provided by an additional cable or additional wires in the 1 MHz feed together with, when necessary, a further line for control functions. The composite output voltage is, in this case, fed directly from the adder 54 to the feeder structure represented by the instrument shaft.

It will be appreciated that losses at UHF are much reduced with this embodiment, to the extent that the power output of the UHF synthesiser may be reduced. Drawbacks include the additional bulk and weight of the handpiece and the possible need for forced fluid cooling of the UHF synthesiser, depending on the required power output. Such cooling could take place by evacuating air from the operation site into a passage at the distal end of the electrode shaft through a filter element to the UHF synthesiser, performing the dual functions of cooling the synthesiser and removing smoke or vapour from the operation site to enhance visibility.

The ability to supply electrosurgical voltages at widely spaced frequencies also has application in a further alternative embodiment making use of a gas plasma electrode, as will now be described with reference to FIG. 10.

It is well known to use an inert gas such as argon, ionised using an r.f. voltage and fed via a nozzle, typically having a diameter in excess of 1 mm, to produce a hot plasma "beam". Directing this gas plasma onto the tissue being treated causes coagulation through transfer of thermal energy.

The behaviour of the argon plasma depends upon the incident energy. The higher the temperature of the argon, the greater its electrical conductivity. Paradoxically, the more energy initially imparted to the plasma the less is the energy absorbed by the plasma due to its lower electrical impedance.

Supplying upper and lower frequency components simultaneously to a plasma-generating electrode assembly has the advantage that formation of the plasma can be performed independently of the conduction of energy along the plasma beam. As described above with reference to FIGS. 1 to 9, the upper and lower components typically have frequencies of 2.45 GHz and 1 MHz respectively.

Figure 10:
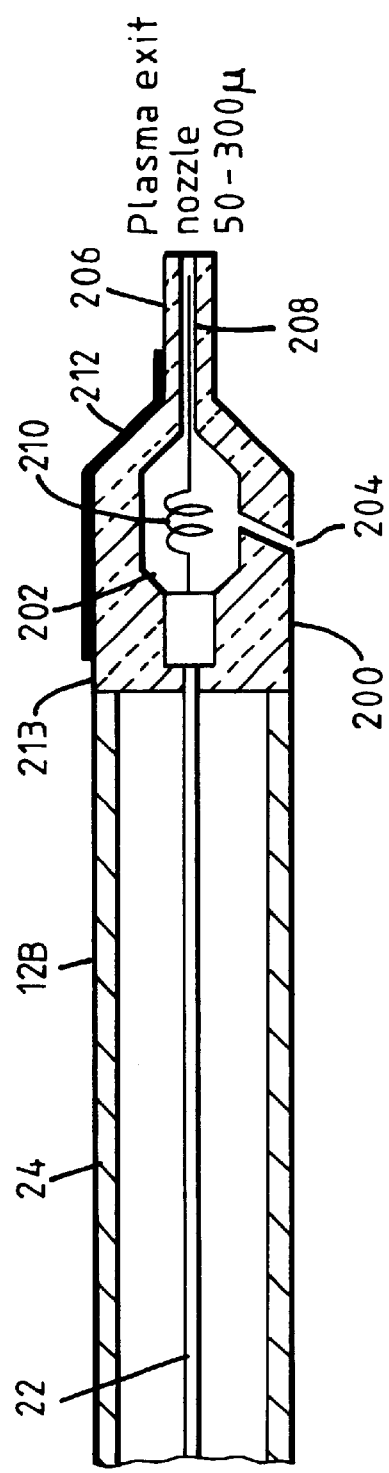
FIG. 10 is a cross-section diagram of an alternative electrode assembly configured for gas plasma generation.

Referring to FIG. 10, the preferred electrode assembly consists of a ceramic nozzle body 200 attached to the end of a coaxial feed structure which has the same configuration as the feed structure in the embodiment described above with reference to FIGS. 1 to 9. Nozzle body 200 has an axial gas supply chamber 202 with a communicating lateral gas inlet 204. The nozzle body 200 is tapered distally to form a narrow tube 206 with an axial bore 208 providing an outlet frown the chamber 202, the exit nozzle having an internal diameter in the region of 50 to 300 $\mu$m. Situated axially within the gas supply chamber 202 and the nozzle bore 208 is a whisker electrode 210 coupled to the inner supply conductor 22 of the coaxial feed. As shown in FIG. 10, the whisker electrode 210 is coiled within the chamber 202 and has an extension extending axially into bore 208 so that the total electrical length of the electrode 210 is about $\lambda/4$ at the frequency of the upper component.

Plated on the lateral exterior surface of the ceramic nozzle body 200 is a conductive return electrode 212 adjacent to the outer supply conductor 24 of the feed structure 12B and spaced from the supply conductor 24 by a gap 213.

Essentially then, the plasma generator comprises a whisker antenna within a ceramic tube having a metallised shroud. The capacitance between the whisker electrode 210 and the return electrode 212 is typically in the region of 0.5 to 5 pF. Clearly, this is a relatively low impedance at 2.45 GHz but a very high impedance at 1 MHz. This, coupled with the fact that the $\lambda/4$ length of the electrode 210 causes the electrode 210 to act as an impedance transformer producing a high voltage at the tip of the electrode, means that the 2.45 GHz component is dissipated within the plasma chamber when an ionisable gas is introduced via inlet 204 (causing plasma generation in bore 208) whereas the low frequency component at 1 MHz is conducted along the plasma beam to target tissue and to earth via the return pad attached to the patient (see FIG. 1).

The plasma generator is highly efficient at UHF frequencies, which means that the plasma may be generated with sufficient flow to absorb as much as 100 watts. The ionised gas is pumped from the chamber 202 through bore 208 which may have a bore as small as 0.1 mms. Since the majority of the power is dissipated within the chamber, little or no power at UHF is conducted to the nozzle outlet by the plasma. Instead, the UHF current component flows from the whisker electrode 210 via capacitive coupling to the return electrode 212, and thence via further capacitive coupling to the outer conductor 24 of the feed structure 12B.

Using the UHF source alone, the plasma beam acts as a powerful tissue coagulation tool, the depth and area of the coagulation effect being determined by the dispersion of the gas beyond the nozzle which depends, in turn, upon the distance the nozzle is held from the tissue surface. This is a purely thermal effect.

As described above, when both lower and upper frequency components are supplied, the lower frequency component at medium frequencies such as 1 MHz (a range of 100 kHz to 5 MHz is applicable in this instance) results in power being conducted along the plasma beam to the target tissue and thence to earth, vaporising the tissue.

Since the 1 MHz component is not coupled in plasma generation, its voltage can be comparatively low, at typically 300 volts to 1000 volts rms. It follows that the ability of the low frequency source to support significant current delivery at low power is superior to that achievable in known prior systems.

The ionising ability of the UHF source is such that gases other than argon may be used Argon has tended to be used in the prior art because it has a low ionisation potential, it is an inert gas, and it is the most abundant of the noble inert gases and consequently the cheapest. However, when using the described electrode assembly, with the plasma beam acting as an active electrode conveying electrosurgical tissue vaporising power at 1 MHz, a significant amount of residual carbon can be produced. This is the result of vaporising the tissue in an oxygen-free environment.

Figure 11:
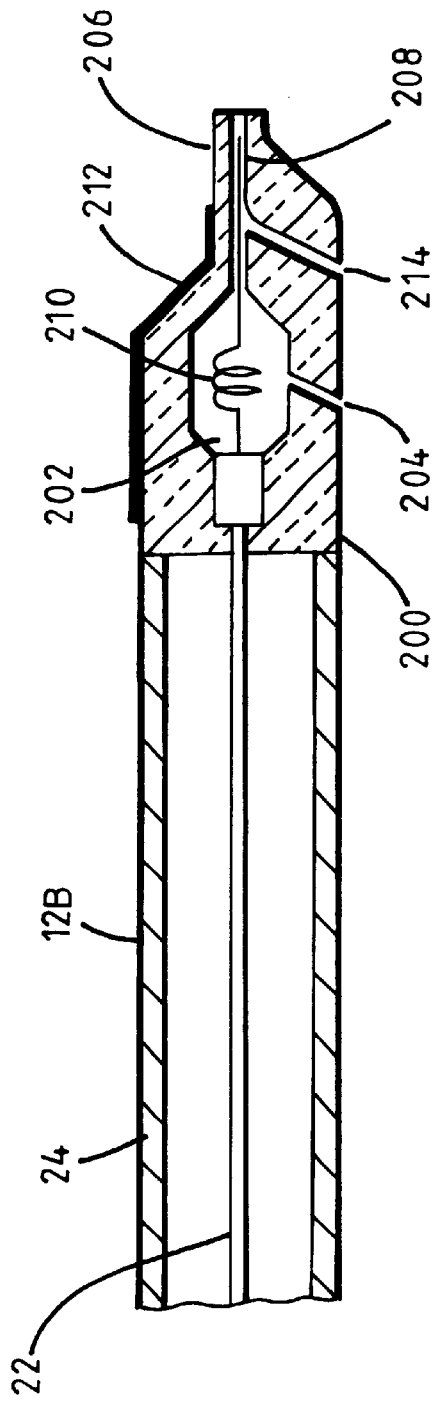
FIG. 11 is a cross-section diagram of a further alternative electrode assembly configured for gas plasma generation.

Use of an oxidising gas plasma by supplying oxygen or an oxide of nitrogen, gases which are both readily available in an operating theatre, counters the formation of carbon Such gases have a considerably higher ionisation potential than argon with the result that considerably higher temperatures are attained with sufficiently conductive plasma streams, to the extent that the gas delivery rate has to be correspondingly reduced. An oxidising gas can be mixed with the argon before plasma generation, and introduced directly via inlet 204. Alternatively, the oxidising gas may be mixed with the argon plasma using an electrode assembly having a second gas inlet, as shown in FIG. 11. The embodiment shown in FIG. 11 makes use of a ceramic body 200 with a second lateral gas inlet 214 communicating with the bore 208 of the nozzle tube 206.

The whisker electrode 210 is preferably tungsten or tantalum due to the high melting point of these metals. Where an oxidising gas is introduced into the plasma generating chamber, a platinum or platinum-coated electrode is more appropriate, in order to avoid electrode oxidisation. The electrode may also be constructed from a thoriated alloy such as a thorium-toungsten alloy to improve electron emission and to promote predictable ionisation.

Dual frequency operation of a gas plasma electrode assembly as described above avoids the difficulties created by generating the plasma and the tissue effects from the same electrical source. Consequently, the difficulty in generating a plasma from a voltage which varies due to large variations in load impedance is avoided, and the lower frequency r.f. source can be used to deliver current through the plasma without relatively high peak voltages when using low frequencies, which places high power demands upon the r.f. generator.

Narrow jet diameters, as disclosed above, as allowed by high excitation voltages and low impedance, result in higher current density upon tissue contact, giving the opportunity to perform rapid but fine tissue vaporisation.

What is claimed is:

1. An electrosurgical system comprising an electrosurgical generator, a feed structure and an electrode assembly, the electrode assembly having at least one active electrode and at least one adjacent return electrode, each of which is coupled to the generator via the feed structure, wherein the generator and feed structure are capable of delivering radio frequency (r.f.) power to the active and return electrodes in lower and upper frequency ranges, the upper range containing frequencies at least three times the frequencies of the lower frequency range, wherein the generator includes a control circuit responsive to electrical load and operable to cause the delivered power to have a predominant frequency component in the lower frequency range when the load impedance is in an upper impedance range and to have a predominant frequency component in the upper frequency range when the load impedance is in a lower impedance range.

2. A dual frequency electrosurgical system for cutting living tissue, the system being arranged to operate normally in a low frequency cutting or vaporisation mode, but to operate in a UHF coagulation mode in response to detection of a lower than normal load impedance as would typically be encountered when a blood vessel is severed.

3. A system according to claim 2, wherein the system comprises an electrosurgical generator, an electrode assembly and at least first and second supply conductors coupling the electrode assembly to the generator, the electrode assembly comprising at least one active electrode and a capacitive return element adjacent the active electrode, and the active electrode and the return element being coupled to the generator by the first and second supply conductors respectively.

4. A system according to claim 2, arranged to operate predominantly at a first frequency in the range of from 100 kHz to 40 MHz when in the low frequency cutting mode and predominantly at a second frequency above 300 MHz when in the UHF coagulation mode.

5. A system according to claim 4, wherein the first frequency is less than 10 MHz and the second frequency is greater than 1 GHz.

* * * * *